(12) United States Patent
Gonzalez et al.

(10) Patent No.: US 9,186,339 B2
(45) Date of Patent: Nov. 17, 2015

(54) USE OF TRANSCRIPTOME MODIFYING AGENTS AND CHEMOTHERAPY OR RADIOTHERAPY AGAINST CANCER

(75) Inventors: Alfonso Dueñas Gonzalez, México D.F. (MX); Luis Estrada Flores, Col. Torielo Guerra (MX)

(73) Assignees: UNIVERSIDAD NACIONAL AUTONOMA DE MEXICO, Mexico, C.P., Mexico City; PSICOFARMA, S.A. DE C.V., Colonia Toriello Guerra, C.P., Mexico City ( * ) Notice: Subject to any disclaimer, the term of this patent is extended or adjusted under 35 U.S.C. 154(b) by 252 days.

(21) Appl. No.: 12/093,906

(22) PCT Filed: Nov. 16, 2005

(86) PCT No.: PCT/MX2005/000106
§ 371 (c)(1),
(2), (4) Date: Jan. 29, 2009

(87) PCT Pub. No.: WO2007/075077
PCT Pub. Date: Jul. 5, 2007

(65) Prior Publication Data
US 2009/0196851 A1   Aug. 6, 2009

(51) Int. Cl.
*A61K 31/19* (2006.01)
*A61K 31/502* (2006.01)
*A61K 45/06* (2006.01)

(52) U.S. Cl.
CPC .............. *A61K 31/19* (2013.01); *A61K 31/502* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 2002/0013367 A1* | 1/2002 | Nau et al. | 514/557 |
| 2004/0116407 A1* | 6/2004 | Borisy et al. | 514/217 |
| 2005/0037992 A1* | 2/2005 | Lyons et al. | 514/49 |
| 2007/0232528 A1* | 10/2007 | Franke | 514/9 |

FOREIGN PATENT DOCUMENTS

WO       WO 03/024442 A2 * 3/2003 ............. A61K 31/19

OTHER PUBLICATIONS

"Histone acetylation and histone deacetylase activity of magnesium valproate in tumor and peripheral blood of patients with cervical cancer. A phase I study," by Chavez-Blanco et al., Molec. Cancer 4, 22-31 (2005).*
"Valproic Acid & Sodium Valproate" in Basic and Clinical Pharmacology, 7th Ed., by Katzung (ed.), Appleton & Lange (Stamford, Conn.), pp. 399-401 (1998).*
"Enhancement of chemotherapy and nitroimidazole-induced chemopotentiation by the vasoactive agent hydralazine" by Siemann, Br. J. Cancer 62, 348-53 (1990).*
"Inhibition of Histone Deacetylase Increases Cytotoxicity to Anticancer Drugs Targeting DNA" by Kim et al., Cancer Res. 63, 7291-300 (2003).*
"The epigenetics of ovarian cancer drug resistance and resensitization" by Balch et al., Am. J. Obstet. Gynecol. 191, 1552-72 (2004).*
"Hydralazine—valproate: a repositioned drug combination for the epigenetic therapy of cancer" by Duenas-Gonzalez et al., Expert Opin. Drug Metab. Toxicol. 10(10), 1433-44 (2014).*
Alma Chavez-Blanco, et al.; Cancer Cell International; Antineoplastic effects of the DNA methylation inhibitor hydralazine and the histone deacetylase inhibitor valproic acid in cancer cell lines; BioMed Central; published Jan. 31, 2006; pp. 1-9; Mexico City, Mexico.
Carlos Perez-Plasencia, et al.; Molecular Cancer; Can the state of cancer chemotherapy be reverted by epigenetic therapy?; BioMed Central; published Jul. 10, 2006; pp. 1-5; Mexico City, Mexico.
Claudia Arce, et al.; Journal of Translational Medicine; Hydralazine target: From blood vessels to the epigenome; BioMed Central; published Feb. 28, 2006; pp. 1-16; Mexico City, Mexico.
Claudia Arce, et al.; A Proof-Of-Principle Study of Epigenetic Therapy Added to Neoadjuvant Doxorubicin Cyclophosphamide for Locally Advanced Breast Cancer; PLoS ONE; published Dec. 20, 2006; pp. 1-11; Issue 1; doi: 10.1371/journal.pone.0000098; Mexico City, Mexico.
M. Candelaria, et al.; A phase II study of epigenetic therapy with hydralazine and magnesium valproate to overcome chemotherapy resistance in refractory solid tumors; European Society for Medical Oncology; Sep. 2007; pp. 1529-1538; vol. 18, No. 9, doi: 10.1093/annonc/mdm204; Mexico City, Mexico.
Alfonso Duenas-Gonzalez; Anti Tumour Treatment; Valproic acid as spigeneti cancer drug: Preclinical, clinical and transcriptional effects on solid tumors; Cancer Treatment Reviews (2008); pp. 206-222; doi: 10.1016/j.ctrv.2007.11.003; Elsevier; Mexico City, Mexico.
Segura-Pacheoco, et al.; Reactivation of Tumor Suppressor Gener by the Cardiovascular Drugs Hydralazine and Procainamide and their Potential use in Cancer Therapy; Clinical Cancer Research, 2003, vol. 9; pp. 1596-1603.
Chaplin, DJ., et al.; Rduction of Tumor Blood Flow by Vasoactive Drugs: A Role in Cnacer Therapy; Biomed Biochim. Acta, 1989, vol. 48, 2/3; pp. S264-S268.

* cited by examiner

*Primary Examiner* — Theodore R West
(74) *Attorney, Agent, or Firm* — Miller, Matthias & Hull LLP

(57) ABSTRACT

The use of transcriptome-modifying agents is disclosed in order to prevent malignant cells from undergoing the necessary genetic changes in order to combat cell insult and survive chemotherapy or radiotherapy. The combination of transcriptome-modifying agents comprises agents that inhibit the DNA methylation machinery plus a substance that inhibits histone deacetylation. A treatment kit is disclosed which includes an effective dose of hydralazine and valproic acid or a salt of same in the case of magnesium valproate, which is intended for use with radiotherapy or chemotherapy in the treatment of patients cancer.

7 Claims, 9 Drawing Sheets

USE OF TRANSCRIPTOME MODIFYING AGENTS AND CHEMOTHERAPY OR RADIOTHERAPY AGAINST CANCER

CROSS-REFERENCE TO RELATED APPLICATIONS

This application is a U.S. national stage filing of International Patent Application No. PCT/MX2005/00106 filed on Nov. 16, 2008.

FIELD OF THE DISCLOSURE

The use of transcriptome-modifying agents is disclosed to assist in the treatment of malignancies by preventing the malignant cells from realizing the gene changes necessary to confront the cellular insult and to survive the chemotherapy or radiotherapy. More specifically the disclosure is related to the combined use of transcriptome-modifying agents that inhibit the machinery of DNA methylation and histone deacetylation, and even more specifically it is related to the use in combination by means of a treatment kit comprising hydralazine and valproic acid or any salt thereof such as magnesium valproate to assist with the treatment of the cancer jointly with chemotherapy or radiotherapy.

BACKGROUND OF THE DISCLOSURE

Cancer or malignancies can be classified as solid or hematopoietic. Examples of the first ones include cancer such as breast, head and neck, colon and rectum cancer, among others. Examples of the hematologic type include leukemia and lymphomas. The DNA in the cellular nucleus exists arranged in chromatin, and has several levels of order. The constitutive unit of chromatin is the nucleosome that consists of octameric nuclear proteins known as histones and on which the DNA winds. The arranging or packing of DNA in the nucleosomes plays an important role for gene regulation. Covalent modifications of histones such as acetylation, play a fundamental role for chromatin regulation and gene expression (Cho K S, Elizondo L I, Boerkoel C F: *Advances in chromatin remodeling and human disease. Curr Opin Genet Dev* 2004; 14:308-15).

Currently, cancer remains as a significant health problem world-wide, according to the International Cancer Research Agency and to World Health Organization, the incidence of this disease is increasing dramatically, with an estimation that of 10 million new cases that were observed in the year 2000, in 20 more years there will be 15 millions. (Mignogna M D, Fedele S, Russo L L. *The World Cancer Report and the burden of oral cancer. Eur J Cancer Prev.* 2004; 13: 139-42). On the other hand, the survival of patients suffering from the most common cancers such as lung, prostate and breast cancer has improved discreetly in the last years. The survival to 5 years was 50% in 1974 and it increased to 63% in the period from 1992 to 1999 (Jemal A, Murray T, Ward E, Samuels A, Tiwari R C, Ghafoor A, Feuer E J, Thun M J. *Cancer statistics, 2005. CA Cáncer J. Clin.* 2005; 55:10-30).

Although the advances in the forms of treatment have allowed small benefits regarding survival, the results are still far from being optimal. At present, chemotherapy together with surgery and radiotherapy are still the fundamental pillar of treatment since the immense majority of patients with cancer need this form of therapy.

The vast knowledge generated on the molecular basis of cancer in the last years, has permitted the design of new forms of therapy that generally are directed to block the function of oncogenes or to reactivate the expression of suppressive genes. Exemplary of these efforts are the use of monoclonal antibodies against some oncogenic receptors such as EGFR, HER2, etc. In case of the suppressive genes, some therapeutic efforts are the use of recombinant adenovirus harboring the coding gene to the functional product of p53 (Hermiston T W, Kirn D H. *Genetically based therapeutics for cancer: similarities and contrasts with traditional drug discovery and development. Mol Ther.* 2005; 11:496-507).

Generally speaking, we can call to this new form of cancer as directed to a single gene product or single gene therapy. However, this approach has severe drawbacks because the malignant cell genome is tremendously adaptable and because the nature of cancer is of multiple steps, therefore, there does not exist a single genetic alteration responsible for the development of the malignant phenotype. This mean that, although the blocking or restitution of a gene or its product can produce an important antitumoral effect, said effect is not supported since with all certainty, the malignant cell eventually will develop resistance against said therapy since the malignant cell will increase or decrease the expression of genes than can accommodate the effect caused by said therapy (Ross J S, Schenkein D P, Pietrusko R, Rolfe M, linette G P, Stec J, Stagliano N E, Ginsburg G S, Symmans W F, Pusztai L, Hortobagyi G N. *Targeted therapies for cancer 2004. Am J Clin Pathol.* 2004; 122:598-609).

At present, it is well known that malignant cells have multiple defects, namely mutations, deletions, duplications, amplifications, as well as epigenetic changes, the latter being stable functional changes due mainly to chromatin modifications, the two more important changes being DNA methylation and histone acetylation. Epigenetic changes must be in a certain state and act in a perfect functional balance to maintain the "malignant homeostasis". This concept is very important since all the defects of the malignant cells are not simply summations, this is consistent with the fact that the proteins coded by the genes play multiple rolls in networks of complex and interactive functions that shows controls of positive and negative feedback. In addition, through the multiple steps process that occurs in tumor generation, the cell should maintain a steady state between the positive and negative signals both from the oncogenic routes and from suppressive genes, to assure that the processes of proliferation and cellular death occur according to the malignant state dynamics (Weinstein I B. *Cancer. Addiction to oncogenes—the Achilles heal of cancer. Science.* 2002; 297(5578):63-4).

In addition to the inherent complexity of global genic expression of malignant cells, the picture is much more complicated when trying to regulate the genic expression as a consequence of exogenous stimuli, particularly from the effect of chemotherapy or radiotherapy. Chemotherapy and radiotherapy produce immediate changes in genic transcription, and these changes occur not only in those genes primarily relevant to the carcinogenic process but also in genes that do not take part directly, such as those involved in metabolism, transport, etc. (Alaoui-Jamali M A, Dupre I, Qiang H. *Prediction of drug sensitivity and drug resistance in cancer by transcriptional and proteomic profiling. Drug Resist Updat.* 2004; 7:245-55). The most important aspect, however, is that only those cells capable of having an adequate transcriptional response to the harmful stimulus are the only ones that will survive the insult. Clearly, in order for this response "adapted" to survive occurs, it is indispensable that the epigenetic mechanisms that regulate transcription are intact. Therefore, if the malignant cell is under the influence of transcriptome-modifying agents, the transcriptional response necessary for survival will not occur and the cell might have functional irreversible changes or suffer apoptosis. The transcription of eukaryotic cells can be defined as the ability of said cells to express biologically active proteins. Therefore, the transcription is a highly regulated phenomenon. The process initiates at gene level and terminates at protein level and involves multiple events; hence the transcription has several levels of regulation among which they are the following: 1) chromatin structure, which is the physical structure of DNA that includes the level of chromatin packing which determines the ability of regulatory proteins to bind to gene regulatory or promoter regions, 2) control of initiation of transcription, 3) transcript transport, 4) transcript processing and modification, 5) transcript stability, 6) translation initiation, 7) post-translational changes, and 8) the transport and stability of the protein. (Archambault J, Friesen J D. *Genetics of eukaryotic RNA polymerases I, II, and III. Microbiol. Rev.* 1993; 57:703-24). Undoubtedly, the transcriptional effects will be more important if acting higher on the level of transcription regulation. Thus the transcriptome-modifying agents, by acting in the highest level of regulation, will have an effect on the overall genic expression of great magnitude.

Covalent modifications of histones, such as acetylation, and DNA methylation, have an essential role in determining the grade of chromatin packing and finally in determining the overall genic expression; because of that, the agents that inhibit DNA methylation and histone deacetylation have demonstrated to have the property of altering significantly the expression. The loss of methylation might reduce the number of protein complexes that bind to methylated domains in certain locus, leading to a decrease of histone deacetylases activity to which the histone deacetylase-inhibiting agent would have to inhibit. Also, the loss of transcription-repressing complexes can favor the re-association of gene promoters with transcription-activating complexes possessing histone acetylase activity. It is known that the most abundant form of DNA methyl transferase (DNMT1) can bind directly to histone deacetylases and that the amino terminus also has the ability to bind co-repressors {Nakao M. *Epigenetics: interaction of DNA methylation and chromatin. Gene.* 2001; 278: 25-31; Robertson K D. *DNA methylation and chromatin-unraveling the tangled web. Oncogene.* 2002; 21:5361-79).

Although hundreds of potential antitumoral agents had been tested, the treatment of the human cancer is still challenging, with many of the antitumoral treatments being only partially effective and with the potential of causing collateral effects to practically all the systems. Therefore, there is the need not only to have more effective therapeutic options but also to have some more specific therapies that attack the malignant cells in a more selective way on the genic transcription. For this reason, one of the objects of the present invention is to provide a composition to assist with the treatment of the cancer based on the alteration of the transcriptome by means of the use of transcriptional modifying agents such as hydralazine and magnesium valproate, with which the cells will become unable to survive to harmful stimulus induced by chemotherapy o radiotherapy.

The antihypertensive agent hydralazine is a DNA methylation inhibitor that has been used to hypomethylate T cell DNA in experimental systems which makes these cells autoreactive (Yung R, Chang S, Hemati N, Johnson K, Richardson B. *Mechanisms of drug-induced lupus. IV. Comparison of procainamide and hydralazine with analogs in vitro and in vivo. Arthritis Rheum.* 1997; 40:1436-43). More recently, it has been demonstrated that hydralazine produces demethylation of promoter region from suppressive suppressive genes and induces its reactivation in vitro and in vivo models; and also, the genic products reactivated are functional (Segura B, Trejo-Becerril C, Pérez E, Chavez A, Salazar A M, Lizano M, Dueñas-González A. *Reactivation of tumor suppressor genes by the cardiovascular drugs hydralazine and procainamide and their potential use in cancer therapy. Clin Cancer Res.* 2003; 9: 1596-603).

Hydralazine has direct inhibitory effects on DNA methyl transferase, and in an in vitro model it has been demonstrated that two nitrogen atoms of the molecule interact with the amino acids Lys162 and Arg240 of enzyme active site which accounts for the demethylating and reactivating properties of the function of suppressive genes (Angeles E E, Vazquez-Valadez, V H, Vasquez-Valadez O, Velazguez-Sanchez A M, Ramirez A, Martinez L, Diaz-Barriga S, Romero-Rojas A, Cabrera G, Lopez-Castañares R, Duenas-Gonzalez A: *Computational studies of 1-hydrazinophthalazine (Hydralazine) as antineoplasic agent. Docking studies on methyltransferase. Letters Drug Design Discovery* 2005; 4:282-286).

Valproic acid or its salts, as in the case of magnesium valproate known also as VPA, 2-propylpentanoic acid is a drug that has been used as anticonvulsivant for many years with a well demonstrated safety profile. (Perucca E: *Pharmacological and therapeutic properties of valproate: a summary after 35 years of clinical experience. CNS Drugs* 2002, 16:695-714). Recently it has been demonstrated that this medicament is an inhibitor of histone deacetylases. The inhibited enzymes are those of the I and II family class the with exception of the histone desacetylases 6 and 10. Hyperacetylation of histones H3 and H4 observed in vitro and in vivo accompanies its enzymatic inhibitory effect on this family of enzymes. This action on histones produces an important effect on induction of differentiation, induction of apoptosis and inhibition of cellular proliferation (Gurvich N, Tsygankova O M, Meinkoth J L, Klein P S: *Histone deacetylase is a target of valproic acid-mediated cellular differentiation. Cancer Res* 2004, 64:1079-1086).

For this reason, another treatment kit is disclosed that includes hydralazine and valproic acid or any of its salts such as magnesium valproate, which contributes to the usual therapy used against cancer.

DETAILED DESCRIPTION OF THE PRESENTLY PREFERRED EMBODIMENT

Figure 1:
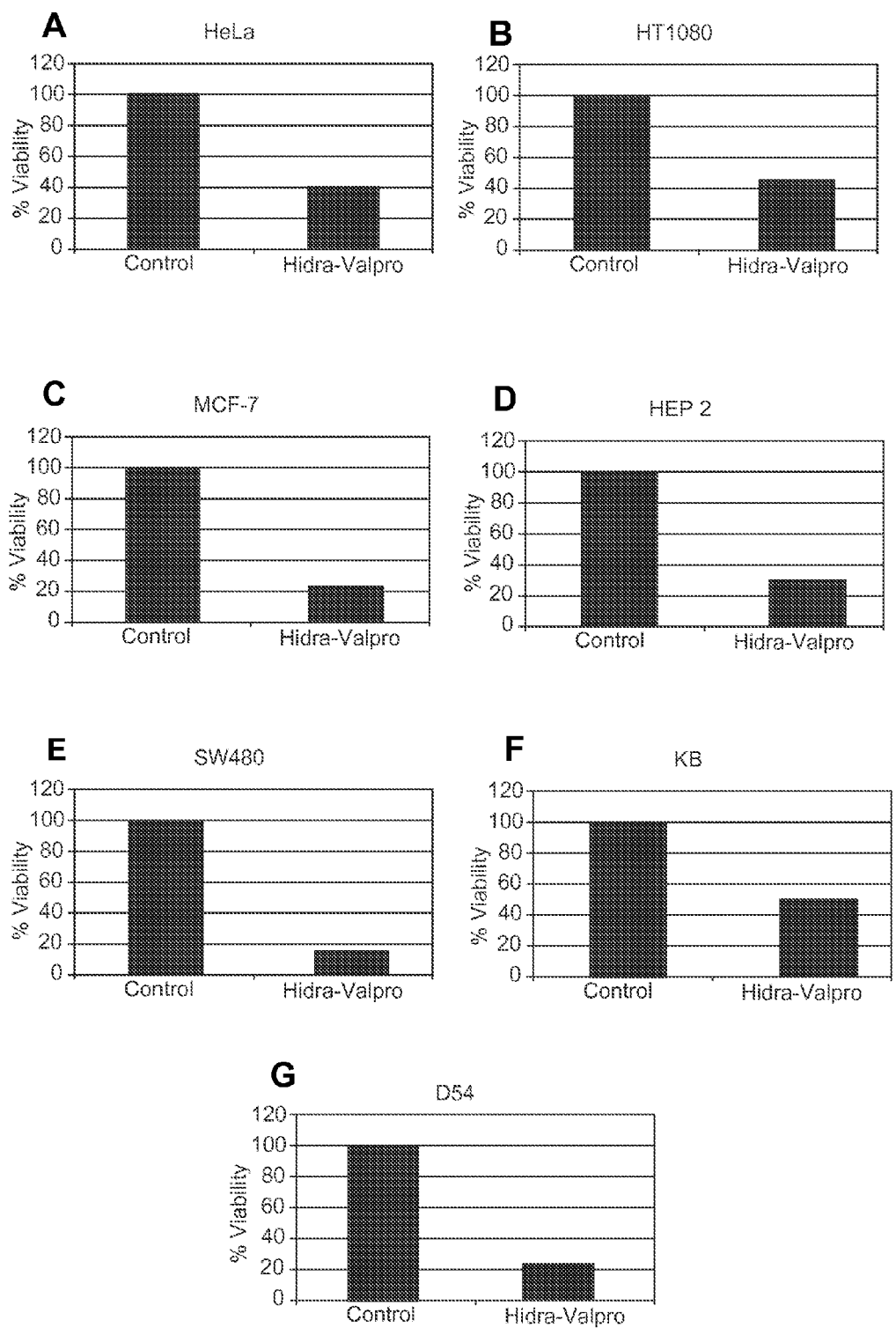
FIGS. 1A, 1B, 1C, 1D, 1E, 1F, and 1G, show the cytotoxic effect in different malignant cell lines treated the disclosed transcriptome modifying composition of present invention.

The use of a composition and a treatment kit is disclosed to assist in the treatment of malignancies by means of the use of transcriptome modifying compounds that complement the treatment with chemotherapy or radiotherapy.

The disclosed composition of transcriptome modifying agents is the combination of hydralazine and valproic acid or any of its salts, such as magnesium valproate, which assists in the chemotherapy which can be, but not limited to these compounds, chlorambucil, cyclophosphamide, iphosphamide, mechlorethamine, melphalan thiotepa, carmustine, lomustine, altretamine, dacarbazine, and procarbazine, cisplatin, carboplastin and oxaliplatin, doxorubicin, daunorubicin, epirubicin, idarubicin, mitomycin C, bleomycin, dactinomycin, retinoids, hormone agents, vincristine, vinblastine, vindesine, vinorelbine, irinotecan, topotecan, etoposide, teniposide, paclitaxel, docetaxel, 5-fluorouracil, gemcitabine, methotrexate, interleukins, interferons, monoclonal antibodies such as trastuzumab, cetuximab, rituxan, myelotarg, and inhibitory small molecules such as gefitinib, erlotinib, and imatinib.

The disclosed composition and treatment kit can be used against several tumor types including, but not limited to, breast, ovary, uterine, skin, bone, prostate, liver, kidney, lung, brain, head and neck, gall bladder, pancreas, colon and rectum, parathyroids, thyroid gland, adrenal glands, stomach, kidney cancer, pheochromocytoma, Wilms tumor, testicle cancer, nueroblastoma, sarcoma, acute and chronic leukemia, lymphomas and myelodysplasic syndromes.

The disclosed composition can be administered by oral route or by any other route of administration in a formulation comprising 83 mg of hydralazine plus valproic acid or a salt thereof such as magnesium valproate at a dose of 30 mg/Kg of weight if the individual exhibits slow acetylation or at a dose of 182 mg of hydralazine plus valproic acid or a salt thereof such as magnesium valproate at a dose of 30 mg/Kg of weight if the individual exhibits rapid acetylation. Both agents in any of their embodiments should be administered in a formulation of controlled release initiating with its administration 7 days before the first dose of chemotherapy or the first radiotherapy session, to allow the modification of transcriptoma prior to the cytotoxic insult of these treatments.

EXAMPLES

Example of Use 1

To demonstrate that the transcriptome modifying composition, hydralazine and valproic acid or magnesium valproate has antitumoral effects, a variety of cellular malignant lines from cervicouterine cancer, breast, colon, upper respiratory and digestive tract cancer, and sarcoma were used. The cells were plated in 96-well plates (Falcon Becton Dickinson, Franklin Lakes, N.J.) at a density of $1.5$-$2.5\times10^3$ cells/well in 0.1 ml of complete media. The following day the cells were treated with hydralazine at 10 µM and magnesium valproate at 1 mM for 4 days. The following day, cellular viability was measured using a MTT assay. Briefly, 50 µl of MTT reagent in phosphate buffered solution were added to each well. Viable cells with active mitochondria reduce MTT to a precipitable purple compound—formazan—which dissolves with DMSO adding 150 µl to each well. Thereafter it is read spectrophotometrically on a ELISA reader. All the assays were carried out in triplicate. The cytotoxic effect of each treatment was expressed in the percentage of cell viability relative to the untreated control (% control) which is defined as $[(A_{570nm}$ treated cells$)/A_{570nm}$ untreated cells$)]\times100$.

FIGS. 1A, 1B, 1C, 1D, 1E, 1F, and 1G, show that in all the treated cell lines HeLa, cervicouterine carcinoma cell line; HT1080 from sarcoma; MCF-7 from breast cancer, KB and HEP2 epidermoid carcinomas from larynx and oral cavity respectively; SW480 from colon carcinoma, KB oral cavity epidermoid carcinoma, HEP2 larinx epidermoide carcinoma; D54 the transcriptome modifying composition produced significant cytotoxicity varying from 12.7% to 43.4% reduction in viability.

Example of Use 2

Figure 2:
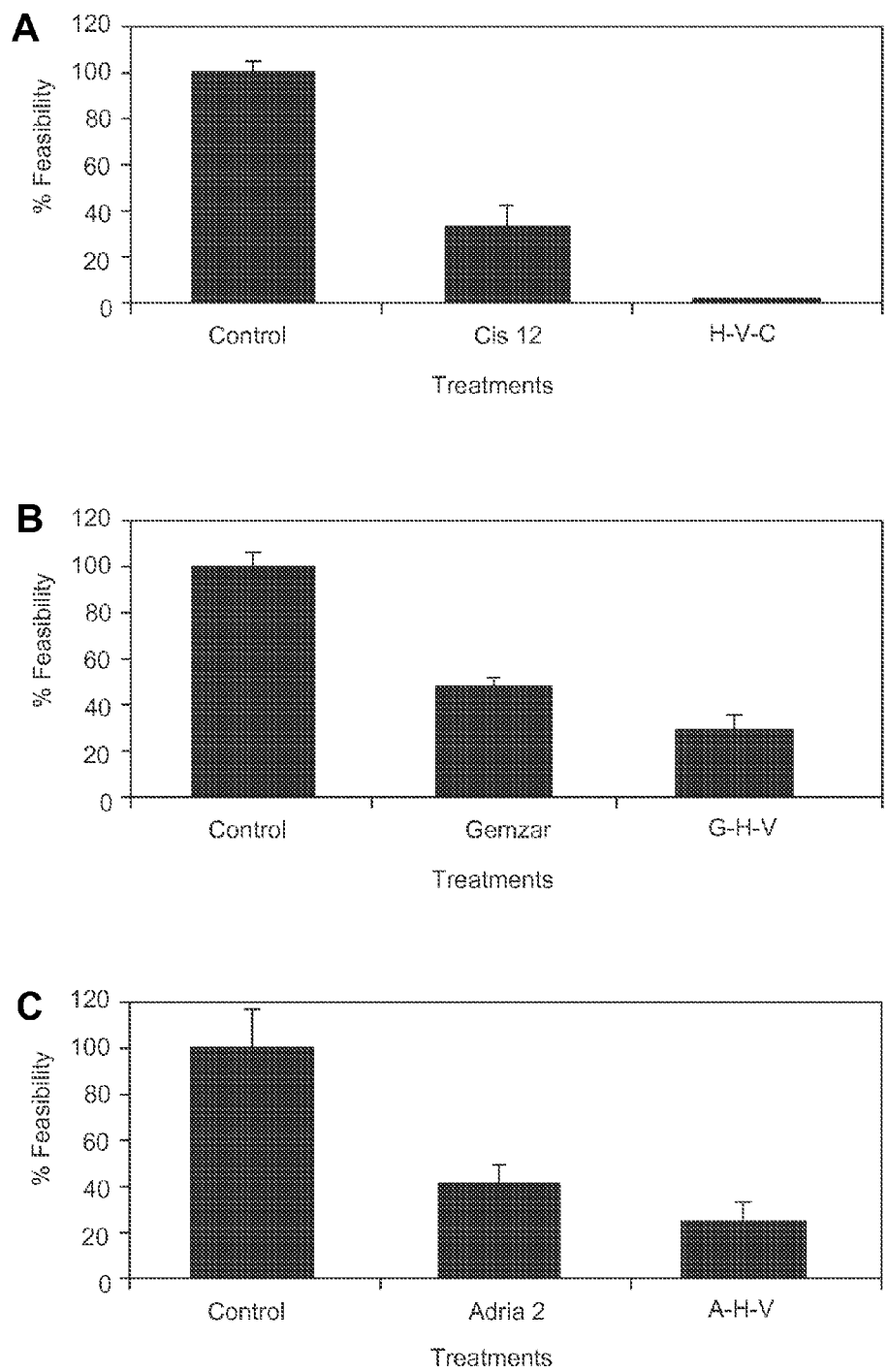
FIGS. 2 A, 2B and 2C show how the transcriptome modifying composition of the present invention produces a potentiation of the cytotoxic effect of representative chemotherapeutic agents (cisplatin, doxorubicin and gemcitabine) in a malignant cell line.

Once demonstrated that the transcriptome modifying composition had inhibitory effects on the growth of the cellular malignant lines, it was investigated whether the composition increased the cytotoxic effect chemotherapeutic agents. With this objective, three drugs were selected that are representative of his class: alkylating agents as cisplatin, antibiotic as doxorrubicin, antimetabolite as gemcitabine. The cells were plated in 96-well plates (Falcon Becton Dickinson, Franklin Lakes, N.J.) at a density of $1.5$-$2.5\times10^3$ cells/well in 0.1 ml of complete media. The following day the cells were treated with the chemotherapeutic agent at the concentration indicated in FIGS. 2A, 2B y 2C plus hydralazine at 10 µM and valproic acid or magnesium valproate at 1 mM. On the next day, the media containing the drugs was removed and fresh hydralazine and magnesium valproate were added at same concentration for another additional 48 hours. On the following day (day 4) cell viability was measured using an MTT assay. Briefly, 50 µl of MTT reagent in phosphate buffered solution were added to each well. Viable cells with active mitochondria reduce MTT to a precipitable purple compound—formazan—which dissolves with DMSO adding 150 µl to each well. Thereafter it is read spectrophotometrically on a ELISA reader. All the assays were carried out in triplicate. The cytotoxic effect of each treatment was expressed in the percentage of cell viability relative to the untreated control (% control) which is defined as $[(A_{570nm}$ treated cells$)/A_{570nm}$ untreated cells$)]\times100$. FIGS. 2A, 2B, y 2C show that in all cases there is a greater cytotoxicity of transcriptome modifying composition plus the chemotherapeutic agent. Under this conditions, a concentration of 12 µM cisplatin, which is a inhibitory concentration 50 (IC50), resulted in a viability reducción of 37% in HeLa cells when treated with the transcriptome modifying composition. A similar effect was also demonstrated for adriamycin and gemcitabine for respective reductions of 27% y 37% respectively.

Example of Use 3

Figure 3:
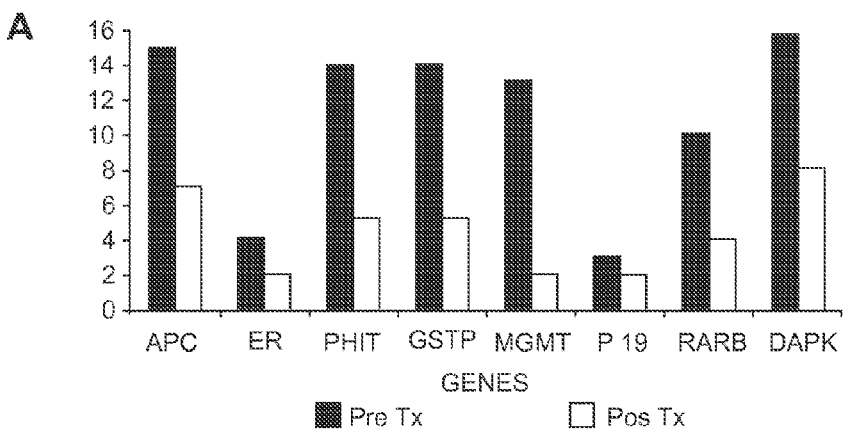
FIG. 3A shows the disclosed methylation frequencies of each gene.
FIG. 3B, shows representative cases of methylation frequencies.
FIG. 3C, shows the correlation between the percentage of methylation and hydralazine dose.
Figure 3:
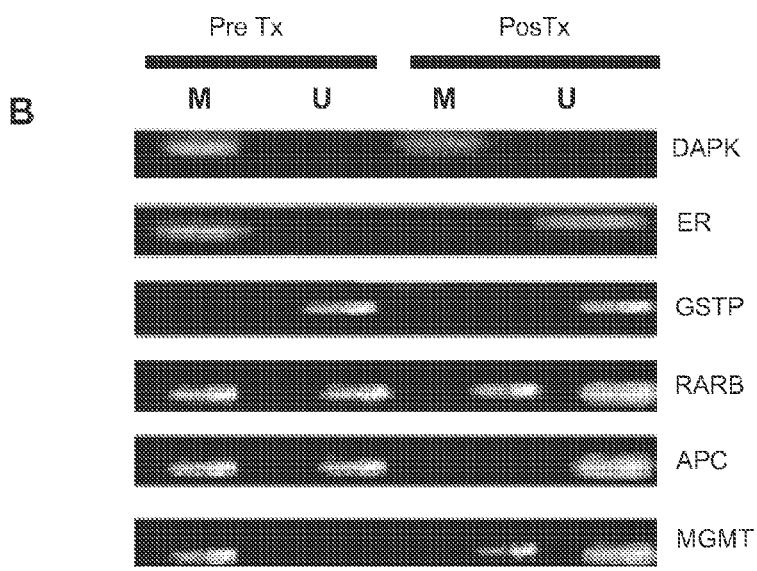
Figure 3:
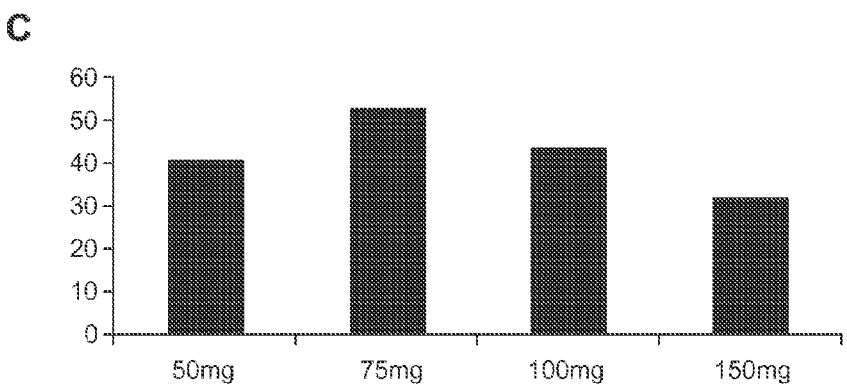

To demonstrate that the demethylating and reactivating effect from the transcription of suppresive genes can be achieved clinically, a phase I clinical study was carried out to demonstrate at which dose hydralazine can have its demethylating and reactivating effect of transcription in cancer patients. Whit this goal, hydralazine was administered to groups of 4 patients each group at doses of: 1) 50 mg/day, 2) 75 mg/day, 3) 100 mg/day and 4) 150 mg/day for 10 days. Biopsies and peripheral blood samples were taken before commencing treatment and at day 11. The state of pre- and post-treatment methylation was analyzed for the promoters of the following genes: APC, MGMT; ER, GSTP1, DAPK, RARβ, FHIT and p16 as well as the state of expression of their messengers by RT-PCR. Also the state of methylation of the gene subject to parental unactivation H19, and a genomic clone which normally is found methylated was evaluated, as well as the global content of methylated citokines in the genome. The toxicity to hydralazine was evaluated using the escale from the U.S. National Cancer Institute (CTC NCI). Hydralazine was well tolerated, only the following undesirable effects were registered: nausea, sickness, fatigue, headache and palpitations. In relation to the genes, it was found that 70% of the samples analyzed (89 of 128) had at least one of the methylated genes in the pretreatment biopsy, 8 genes per each of the 16 biopsies-patients, and that all the patients had at least one methylated gene in their tumors. The individual analysis for each gene demonstrated the following frequencies of methylation: APC 94%, ER 25%, FHIT 88%, GSTP1 88%, MGMT 81%, p16 19%, RARβ 62%, and DAPK 100%. In the post-treatment biopsies it was found a variable frequency of demethylation in each gene, varying from 15% 2 out of 13 samples for MGMT to 67% for the gene p16 2 out of 3. FIG. 3A. Representative cases are presented in FIG. 3B. The correlation between the percentage of demethylation and the dose of hydralazine was as follows: 50 mg 40%, 75 mg 52%, 100 mg 43%, 150 mg 32% as can be seen in FIG. 3C.

Figure 4:
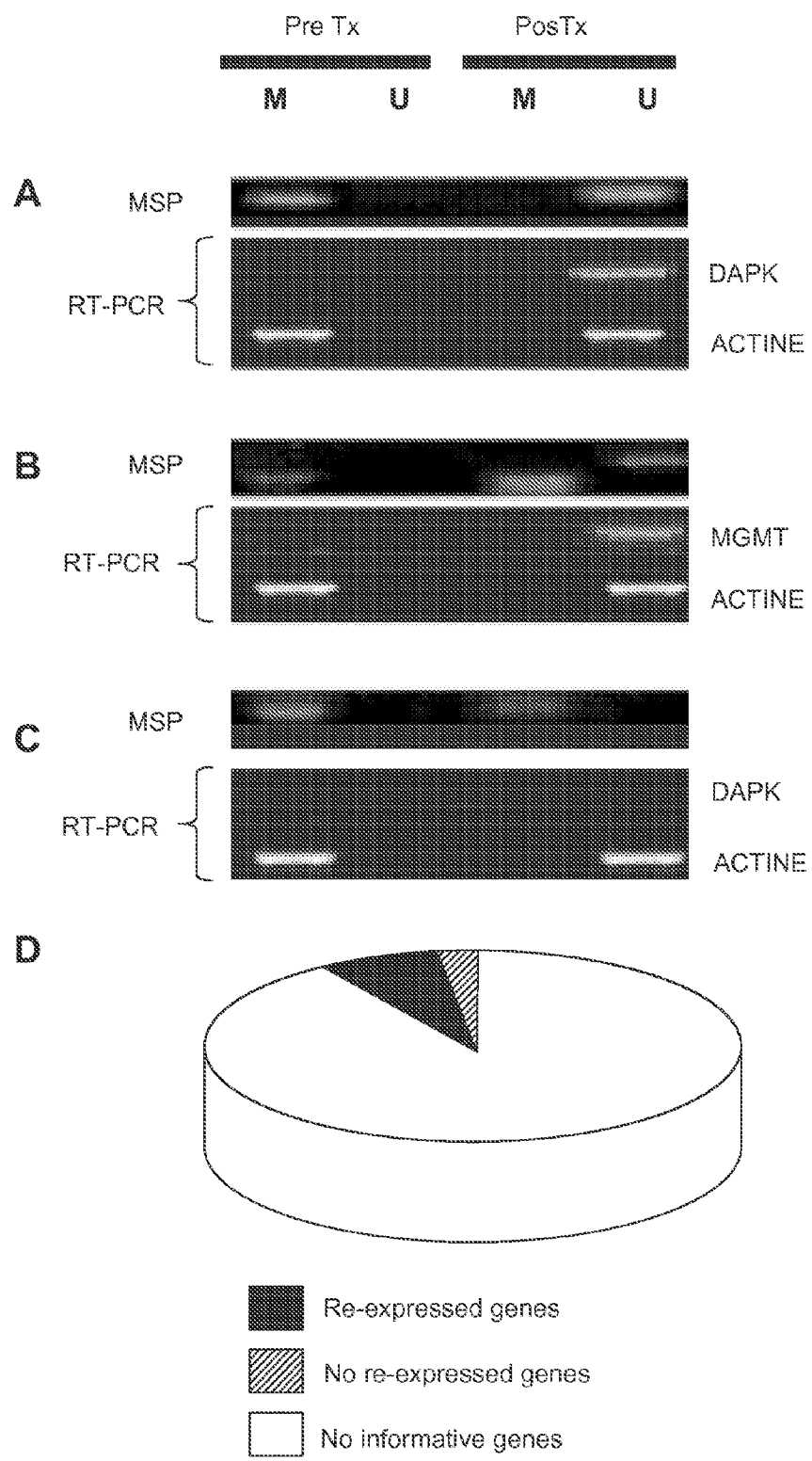
FIGS. 4A, 4B, 4C and 4D show exemplary cases of genic expression of messenger in pre- and post-treatment biopsies.

The analysis of genic expression shows that 90% (116 of 128) of tumor samples expressed the messenger in the pre- and post-treatment biopsy independently of the methylation state of the gene and therefore they were not informative. Of the 12 informative cases it was found that 9 of them did not have expression of the pre-treatment gene being methylated but post-treatment they were demethylated and they re-expressed the gene. The representative cases are shown in FIGS. 4A, 4B, y 4C and the entire frequency of genic re-expression is summarized in FIG. 4D.

The above results demonstrate that hydralazine in a range of dose between 50 and 150 mg is effective to alter the genic expression in patients with cancer (Zambrano P, Segura-Pacheco B, Perez-Cardenas E, Cetina L, Revilla-Vazquez A, Taja-Chayeb L, Chavez-Blanco A, Angeles E, Cabrera G, Sandoval K, Trejo-Becerril C, Chanona-Vilchis J, Duenas-González A. *A phase I study of hydralazine to demethylate and reactivate the expression of tumor suppressor genes.* BMC Cancer 2005; 5:44).

Example of Use 4

Figure 5:
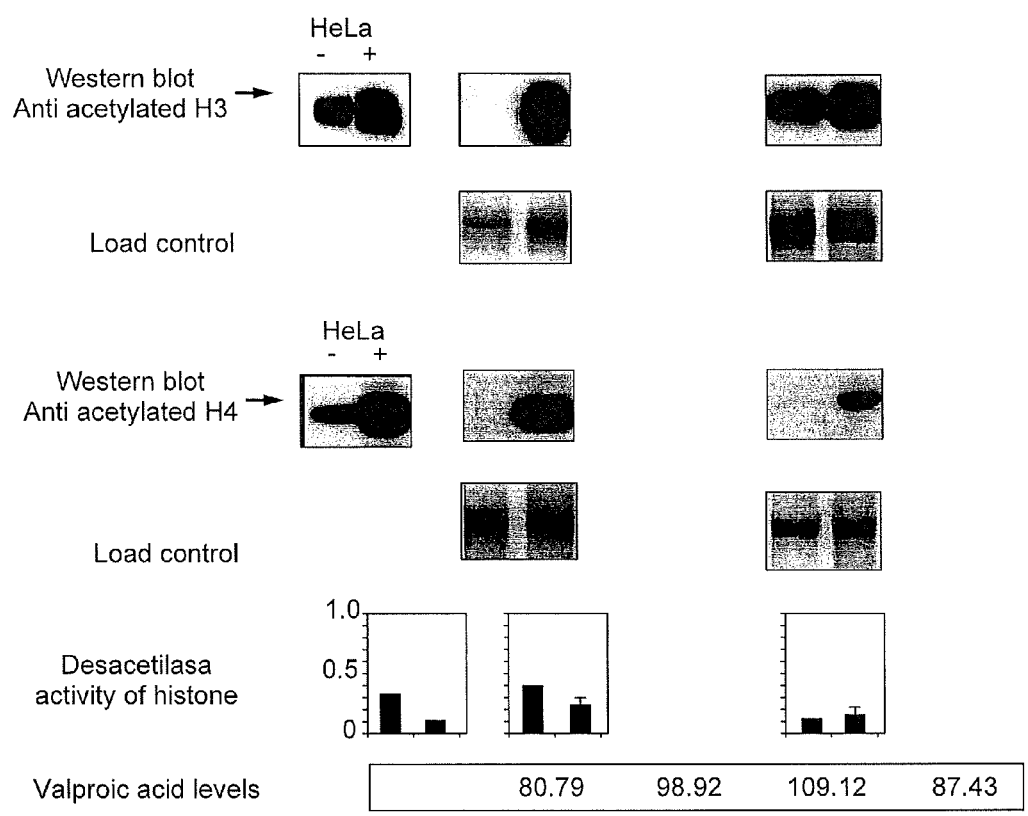
FIGS. 5, 6 and 7 show histone deacetylase activity data.
Figure 6:
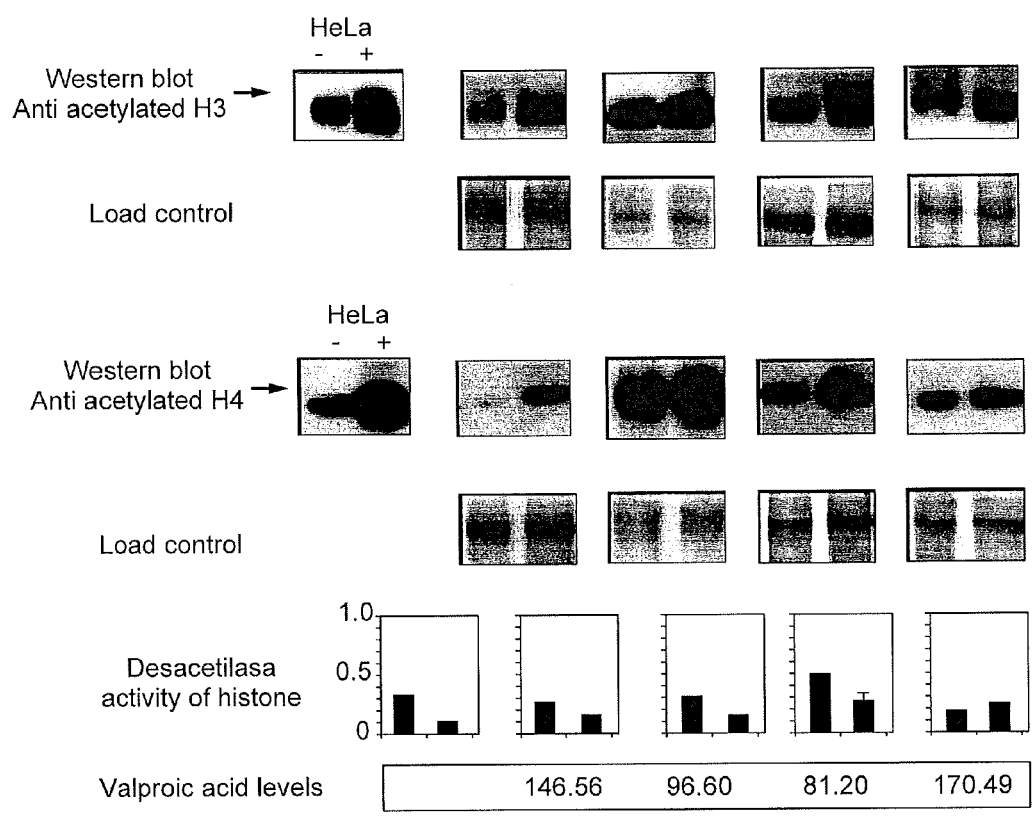
Figure 7:
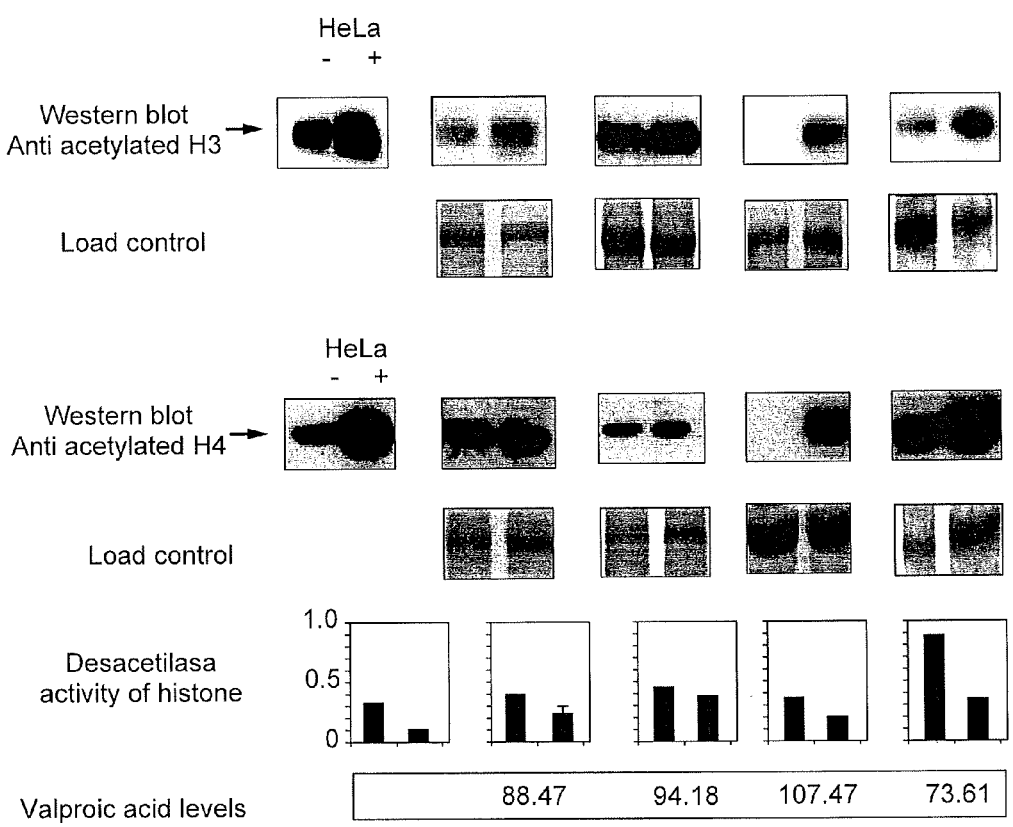
Figure 8:
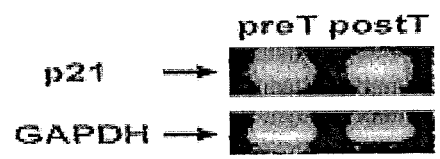
FIG. 8 shows data of the histone deacetylase inhibitory effect of the composition.

To prove that the valproic acid or a salt thereof such as magnesium valproate induces hyperacetylation of histones and inhibition of the activity of histone deacetylases in the tumor of patients with cancer, another clinical study was realized where different doses of valproic acid or a salt thereof such as magnesium valproate were administered to patients with cervicouterine cancer. Twelve patients with this cancer of recent diagnosis and without previous treatment received the following doses of magnesium valproate in groups of 4 patients. Group 1, 20 mg/Kg, Group 2, 30 mg/kg, Group 3, 40 mg/Kg. A biopsy of the tumor and a blood sample were taken before the treatment and on the following day (day 6) since valproic acid or a salt thereof such as magnesium valproate was administered for 5 days in divided doses every 8 hours. The hyperacetylation of Histone H3 was analyzed in the samples and histone H4 in the tumor by Western blot, as well as the activity of histone deacetylases in nuclear extracts of the tumor using a calorimetric essay, as well as the levels of valproic acid in serum. The level of expression of the genes p21 and CAR was also analyzed in the pos-treatment biopsies. The toxicity of the treatment was recorded at the end of the cycle. All the patients completed the treatment; the average dose was of 1890 mg/day with the averages corresponding to the doses of 20, 30 and 40 mg/kg of 1245, 2000 and 2425 mg respectively. Grade 2 drowsiness was observed in nine of the 12 patients. After the treatment, hyperacetylation of H3 and H4 in nine and seven patients respectively, was found; six of them had hyperacetylation in both histones (positive and negative control, HeLa cells treated or not with tricostatine respectively). The activity of histone deacetylases diminished in 8 patients whereas there were no changes in two patients which was statistically significant (two-tailed t test p<0.0264). (Positive and negative control, nuclear extracts of HeLa cells treated or not with tricostatine), FIGS. 5, 6 and 7. This data demonstrates that magnesium valproate at the used doses is effective and well tolerated as inhibitor of histone deacetylases which reflects the changes in the expression of such genes as p21 (FIG. 8) which increases its expression.

Example of Use 5

Figure 9:
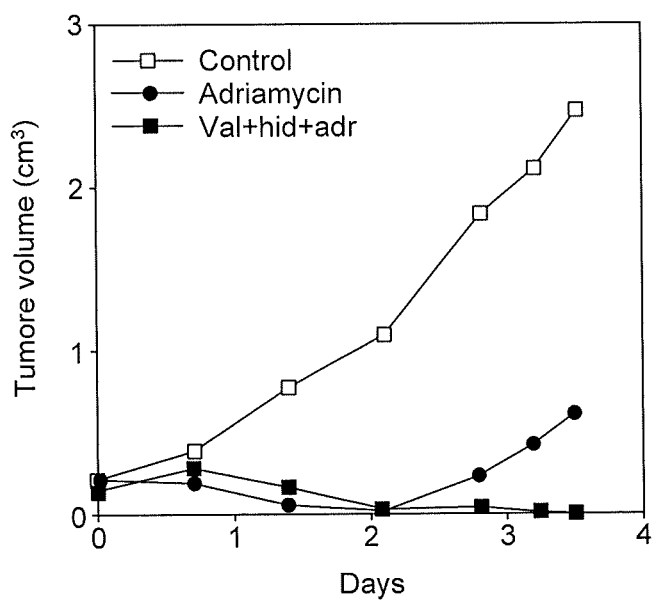
FIG. 9 shows the tumor growth blocking effect in animals with and without treatment with the composition.

Once the capacity of hydralazine and valproic acid or a salt thereof such as magnesium valproate to alter the expression génica in the patients' tumors was assessed, we investigate if the composition of these transcriptome modifying agents increased the antitumoral effect of the chemotherapy in a model of sarcoma in immunodeficient mice. With this goal, groups of 6 female athymic mice were studied, which were injected with 6 million cells of the sarcoma HT1080 cellular line. Once the tumors were formed, the animals were treated systemically with hydralazine and valproic acid or a salt thereof such as magnesium valproate with doses equivalent to those used in the patients. The groups of treatment were as follows: 1) control treated with saline solution, 2) treated weekly with adriamycin, 3) treated with the composition of hydralazine and valproato for 7 days followed by the same weekly treatment with adriamycin. The results demonstrate that at 5 weeks the tumors of the animals without treatment reach a volume of between 2 and 3 cm$^3$, and the treatment with adriamycin produces an almost complete antitumoral effect 3 weeks after treatment, nevertheless from this time the tumors grow again whereas in the animals treated with the composition, the tumor re-growth is blocked as can be seen in FIG. 9. The above suggests that the transcriptome modifying combination prevents the tumor cell from effecting the transcriptional changes necessary to recover the capacity of growth. This phenomenon occurs commonly in the treatment of the cancer in the patients, where often an entire or almost entire antitumoral response is observed to relapse later. The composition of the present invention therefore might induce extended or complete remissions of the tumors.

The disclosed composition can be incorporated in a treatment kit to be administered orally or for by any other route of administration in a formulation comprising 83 mg of hydralazine plus valproic acid or a salt thereof such as magnesium valproate at a dose of 30 mg/Kg of weight if the individual exhibits slow acetylation and at a dose of 182 mg of hydralazine plus valproic acid or a salt thereof such as magnesium valproate at a dose of 30 mg/Kg of weight if the individual exhibits fast acetylation. Both agents should be administered in a controlled release formulation to avoid the peaks in serum levels produced by hydralazine and valproic acid or a salt thereof such as magnesium valproate and to reduce the side effects derived from its rapid absorption.

Since the effect of hydralazine on the inhibition of methylation initiates at least 48 hours after its administration and that the effect of valproic acid or a salt thereof such as magnesium valproate on the transcription could be higher on a background of demethylation, the treatment with the composition preferably must initiate seven days before the first dose of chemotherapy or radiotherapy to allow the modification of the transcriptome before to the cytotoxic insult of the chemotherapy or radiotherapy.

What is claimed is:

1. A pharmaceutical composition comprising:
hydralazine present in an amount selected from the group consisting of about 83 mg for individuals exhibiting slow acetylation and about 182 mg for individuals exhibiting fast acetylation;
valproic acid or a salt thereof present in an amount of about 30 mg/kg;
wherein the hydralazine and the valproic acid or the salt thereof are combined with a pharmaceutically acceptable vehicle for treating cancer.

2. The pharmaceutical composition according to claim 1, wherein the salt of the valproic acid is magnesium valproate.

3. A method treating cancer, the method comprising:
administering the pharmaceutical composition of claim 1 to a patient in need of cancer treatment;
wherein the administering is performed to assist in the treatment of cancer together with chemotherapy or radiotherapy.

4. The method according to claim 3, wherein the chemotherapeutic agent is selected from the group consisting of: chlorambucil; cyclophosphamide; iphosphamide; mechlorethamine; melphalan thiotepa; carmustine; lomustine; altretamine; dacarbazine; procarbazine; cisplatin; carboplastin; oxaliplatin; doxorubicin; daunorubicin; epirubicin; idarubicin; mitomycin C; bleomycin; dactinomycin; retinoids; vincristine; vinblastine; vindesine; vinorelbine; irinotecan; topotecan; etoposide; teniposide; paclitaxel; docetaxel; 5-fluorouracil; gemcitabine; methotrexate; interleukins; interferons; trastuzumab; cetuximab; rituxan; myelotarg; gefitinib; erlotinib; and imatinib.

5. The method of claim 3, wherein said cancer is selected from the group consisting of: breast; ovary; uterine; skin; bone; prostate; liver; kidney; lung; brain; gall bladder; pancreas; colon; rectum; parathyroid; thyroid; adrenal; stomach; kidney; pheochromocytoma; Wilms tumor; testicle; cervicouterine; nueroblastoma; sarcoma; leukemia; lymphoma; and myelodysplasic syndromes.

6. The method according to claim 3, wherein the salt of valproic acid is magnesium valproate.

7. The method according to claim 3, further comprising administering the pharmaceutical composition orally and daily.

* * * * *